June 19, 1934. A. E. SMITH Re. 19,219

AMPULE

Original Filed July 16, 1927

INVENTOR.
A. E. SMITH
BY
ATTORNEY.

Reissued June 19, 1934

Re. 19,219

UNITED STATES PATENT OFFICE 19,219

AMPULE

Arthur E. Smith, Los Angeles, Calif.

Original No. 1,770,220, dated July 8, 1930, Serial No. 206,242, July 16, 1927. Application for reissue July 5, 1932, Serial No. 620,930

4 Claims. (Cl. 128—218)

This invention relates to a medical container or ampule.

The general object of this invention is to provide an improved drug containing ampule wherein the drug is hermetically sealed in the ampule.

Another object of the invention is to provide a drug containing ampule having an improved form of stopper therein for ejecting the contents of the ampule.

A further object of the invention is to provide an ampule having novel means thereon for coacting with a syringe to form a fluid tight seal between the syringe and the ampule.

A specific object of the invention is to provide a novel closure for the discharge end of an ampule.

Other objects and advantages of the invention will be apparent from the following description taken in connection with the accompanying drawing wherein.

Figure 1:
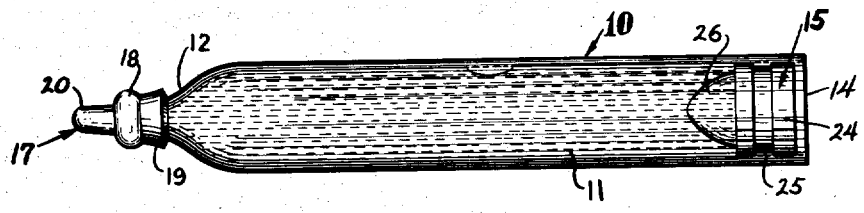
Fig. 1 is a side elevation of my improved ampule.
Figure 2:
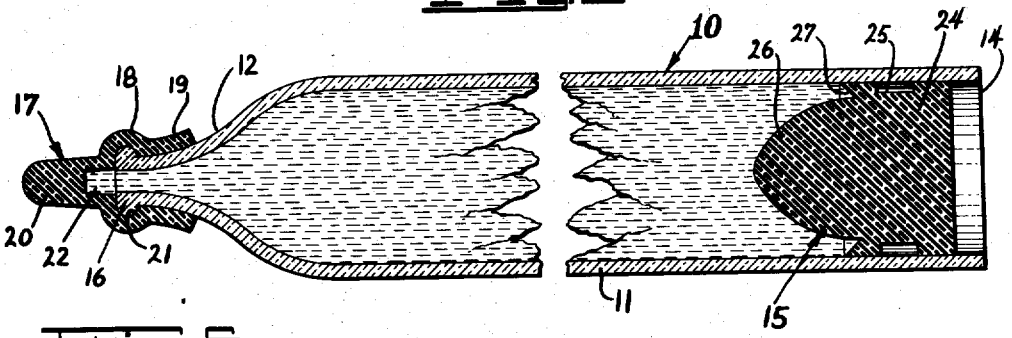
Fig. 2 is an enlarged central longitudinal section through my improved ampule.
Figure 6:
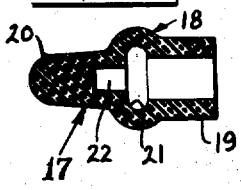
Fig. 6 is a section of the cap.
Figure 3:
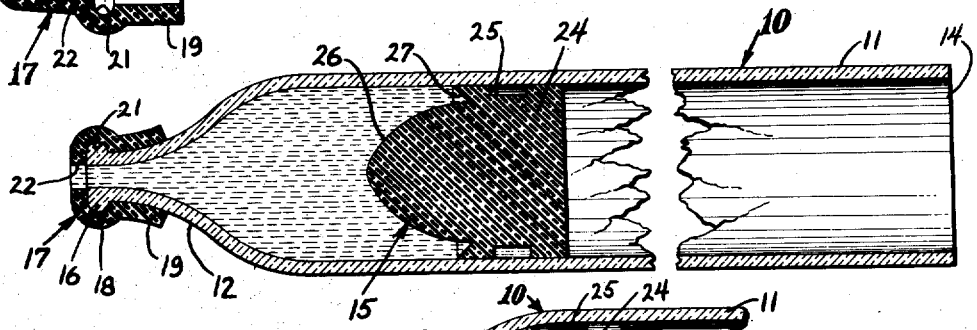
Fig. 3 is a view similar to Fig. 2 with the tip removed from the closure and the stopper moved towards the discharge end of the ampule to eject the contents therefrom.
Figure 4:
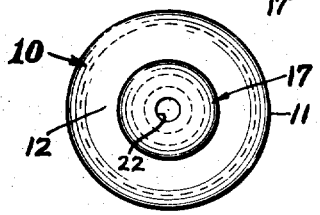
Fig. 4 is a front elevation of the discharge end of the ampule as shown in Fig. 3.

Referring to the drawing by reference characters I have indicated my improved ampule generally at 10. This ampule is primarily adapted for use in a hypodermic syringe of the ampule containing type. The ampule may be of any desired type but is preferably of a size to hold the amount of drug necessary for one injection.

The ampule 10 which is preferably made of glass, comprises an elongated hollow cylindrical body portion 11 terminating at one end in a reduced tapered open ended neck 12. The other end of the ampule is preferably left straight and open as indicated at 14 and is adapted to be closed by a stopper 15.

Adjacent the end of the tapered neck 12 and integral therewith I provide an outer annular bead 16. The open end of the neck 12 is adapted to be closed by a cap 17 which comprises a body portion 18 including a skirt 19 and a reduced tip 20. Within the body portion 18 I may provide an annular groove 21 in which the annular bead 16 on the end of the neck 12 is positioned.

Within the cap I provide a recess 22 which extends into the tip 20 and is approximately the same size as the adjacent opening in the neck 12 of the ampule. The cap is preferably made of a good grade of rubber vulcanized to the desired degree of hardness. When the cap 17 is placed on the ampule it is slightly distorted so that the groove 16 tightly engages the bead 16 and the skirt 19 of the cap tightly engages the tapered neck 12, thus forming a fluid tight seal between the cap and the ampule.

The stopper 15 in the open end 14 of the ampule comprises a body portion 24 provided intermediate its length with an outer annular groove 25. The forward end of the stopper is provided with a protuberant conical tip 26 and a conical groove 27 at the juncture of the tip 26 and the body 24. The groove 27 forms a feather edge on the front face of the body 24 which, when the stopper 15 is moved within the body 11 of the ampule, is forced by the pressure of the fluid to tightly engage the inner walls of the body 11, thus forming a fluid tight seal between the ampule body and the stopper. This seal prevents fluid in the ampule from leaking past the stopper when the contents of the ampule are being ejected.

Figure 5:
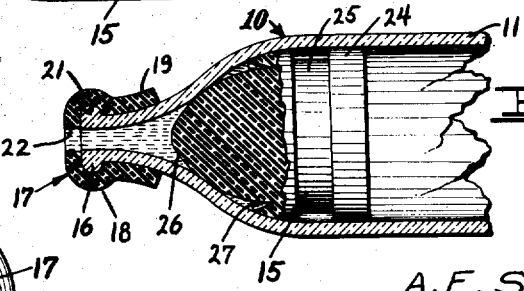
Fig. 5 is a fragmentary central longitudinal section of the ampule showing the stopper moved to its fullest discharge position.

The conical tip 26 of the stopper forces out more of the liquid in the ampule than would a flat ended stopper, since the conical end enters the neck 12 as shown in Fig. 5, thereby assuring an approximately full discharge of the contents of the ampule. The stopper 15 like the cap 17 is preferably made of a good grade of rubber vulcanized to the desired hardness.

To prepare a filled ampule for use it is only necessary to remove the tip 20 of the cap 17 by cutting it at the juncture with the body portion. This exposes the recess 22 which then forms an aperture through which the contents of the ampule may be expelled when the stopper 15 is moved towards the neck 12.

After removing the tip 20 of the ampule cap the ampule may be inserted into the barrel of a syringe, the cap 17 engaging the syringe adjacent the discharge end thereof and the stopper 15 being adapted to be engaged by a plunger rod in the syringe.

To eject the contents of the ampule after it is placed in an operative position in a syringe the stopper 15 is moved within the ampule body 11 towards the neck 12, thus causing the stopper to act as a piston to expel the contents of the ampule.

As pressure is applied on the stopper 15 to expel the contents of the ampule the cap 17 will be forced into very tight engagement with the syringe, the more pressure required to move the stopper the tighter the cap 17 will engage the syringe, thus creating a fluid tight seal between the discharge end of the ampule and the syringe.

The ampule may be filled before or after the cap or stopper is inserted, in any desired manner.

From the foregoing description it will be apparent that I have provided an improved container or ampule which can be economically manufactured and which is highly efficient in use.

Having thus described my invention, I claim:

1. An ampule comprising a hollow body portion constricted at one end to form a tapered neck, an aperture in said neck communicating with the interior of said hollow body, an external bead on said tapered neck, a resilient cap arranged on said neck and engaging the surface of said bead and the front end of said neck, a recess in said cap extending beyond the front end of said neck whereby when a portion of said cap is cut away communication is formed through said cap to the interior of said ampule.

2. An ampule comprising a body portion constricted at one end to form a tapered neck, an external bead on said neck, a resilient cap, said cap including a body portion and a tip, a recess in said body portion fitted over said neck, a second recess in which said bead is positioned, a third recess in said body portion extending into said tip, whereby when said tip is cut away at its juncture with said body portion an aperture is formed through said cap affording communication with the interior of said ampule.

3. An ampule comprising a hollow body, a resilient closure for one end of said body, said closure including a body portion and an integral, reduced, severable tip, means providing a fluid tight joint between said ampule and said closure, said means comprising a resilient peripheral, outwardly extending bead on said closure, one wall of said bead engaging the extreme end of the ampule, said body portion and said tip having communicating recesses, whereby when said tip is severed, an aperture is formed through said closure affording communication with the hollow body of the ampule.

4. An ampule, a closure therefor, said closure comprising a resilient cylindrical body portion directly engaging the ampule, said body having a radially outwardly directed integral portion thereon, said outwardly directed portion directly engaging and substantially covering the entire discharge end face of the ampule to prevent inward movement of the closure away from the discharge end of the ampule and serving to maintain said parts in fluid tight engagement with each other, a reduced integral tip portion on the closure in advance of said outwardly directed portion, said body having a recess therein in communication with the interior of the ampule and said tip having a recess in alignment with the body recess, the outer portion of said tip being removable adjacent to the inner end of the outwardly directed portion, whereby to establish communication between the interior of said ampule through the recess in said tip to the exterior of the ampule.

ARTHUR E. SMITH.